(12) United States Patent
Mastovich

(10) Patent No.: US 8,138,470 B2
(45) Date of Patent: Mar. 20, 2012

(54) CALIBRATION STANDARDS FOR ELECTRON MICROSCOPES AND ELECTRON COLUMN TOOLS

(76) Inventor: John Mastovich, Murrysville, PA (US)

( * ) Notice: Subject to any disclaimer, the term of this patent is extended or adjusted under 35 U.S.C. 154(b) by 0 days.

(21) Appl. No.: 12/720,200

(22) Filed: Mar. 9, 2010

(65) Prior Publication Data

US 2010/0308221 A1   Dec. 9, 2010

Related U.S. Application Data

(60) Provisional application No. 61/158,841, filed on Mar. 10, 2009.

(51) Int. Cl.
*G01D 18/00* (2006.01)

(52) U.S. Cl. .................................................. 250/252.1
(58) Field of Classification Search ............... 250/252.1
See application file for complete search history.

(56) References Cited

U.S. PATENT DOCUMENTS 5,858,781 A * 1/1999 Matyas et al. ................ 435/369

* cited by examiner

*Primary Examiner* — Kiet Nguyen
(74) *Attorney, Agent, or Firm* — Eckert Seamans Cherin & Mellott, LLC; Arnold B. Silverman, Esquire

(57) ABSTRACT

A calibration standard structured to obtain both morphology and chemistry information with respect to particles analyzed simultaneously. The standard is structured to verify the accuracy of the data obtained in the particle analysis. Related methods of manufacture and use are provided.

4 Claims, 9 Drawing Sheets

Photo resist application Level 1

Photo resist development

Lift Off

Table 1
Region A: Large Particles/Low Density

| Diameter μm | # Fields | # Particles |
|---|---|---|
| 1.0 | 100 | 250 |
| 2.0 | | 250 |
| 5.0 | | 250 |
| 10.0 | | 250 |
| Total | | 1000 |

Table 2
Region B: Large Particles/High Density

| Diameter μm | # Fields | # Particles |
|---|---|---|
| 1.0 | 100 | 2500 |
| 2.0 | | 2500 |
| 5.0 | | 2500 |
| 10.0 | | 2500 |
| Total | | 10000 |

Table 3
Region C: Small Particles/Low Density

| Diameter μm | # Fields | # Particles |
|---|---|---|
| 0.1 | 100 | 250 |
| 0.2 | | 250 |
| 0.5 | | 250 |
| 1.0 | | 250 |
| Total | | 1000 |

Table 4
Region D: Small Particles/High Density
| Diameter μm | # Fields | # Particles |
| --- | --- | --- |
| 0.1 | 100 | 2500 |
| 0.2 | | 2500 |
| 0.5 | | 2500 |
| 1.0 | | 2500 |
| Total | | 10000 |
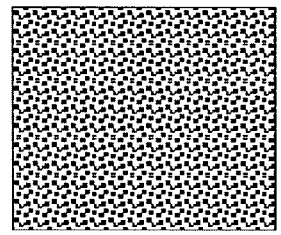
Figure 11
Table 5
Region E: Two-Phase Particles
| Diameter μm | # Fields | # Particles |
| --- | --- | --- |
| 1.0 | 5 | 100 |
| 5.0 | | 100 |
| 10.0 | | 100 |
| Total | | 300 |
Figure 12
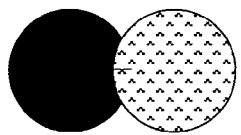
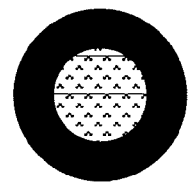
Figure 12(a)  Figure 12(b)

CALIBRATION STANDARDS FOR ELECTRON MICROSCOPES AND ELECTRON COLUMN TOOLS

BACKGROUND OF THE INVENTION

1. Field of the Invention

The present invention relates to calibration standards, and more specifically, standards which, in particle analysis, provide simultaneous morphology and chemistry.

2. Description of the Prior Art

In particle analysis by way of electron beam tools, it has been known to employ standards for either determination of morphology or chemistry, but not both simultaneously.

Lacking in the prior art is the ability to place specificity on the size, shape, chemistry, and location at one time on the standard.

There remains, therefore, a very real and substantial need for standards which provide simultaneous, accurate information regarding both morphology and chemistry in particle analysis.

SUMMARY OF THE INVENTION

The present invention has provided a method of making such standards and using the same with the model to be changed to fit specific application requirements.

The product design will preferably be built employing a semiconductor fabrication process in order to provide the structures in the systematic layout, shapes, and sizes required. The standard can then be modified to be used with various electron column tools, such as, for example, scanning transmission electron microscope.

It is an object of the present invention to provide an efficient and economical method of manufacturing standards for use in particle analysis by way of electron column tools with simultaneous determination of morphology and chemistry.

It is a further object of the present invention to provide such standards by a semiconductor fabrication process.

It is another object of the present invention to provide such a standard which will verify the analysis and allow the analyst to speed the analysis of a point of verifying that the data remains accurate and reproducible.

It is a further object of the present invention to provide such enhanced speed as compared with known prior art comparative analysis on the sample in an iterative manner, which lacks the ability to compare or verify with a known standard.

It is a further object of the present invention to provide a single standard which can be analyzed in a wide range of spectrometers, electron column tools, and x-ray column tools.

It is another object of the present invention to provide a standard which facilitates enhanced speed accuracy and cost-tool advantages and relates to existing RJ Lee patent property.

These and other objects of the present invention will be more fully understood from the following description of the invention with reference to the drawings appended hereto.

BRIEF DESCRIPTION OF THE DRAWINGS

FIGS. 8-11 illustrate variations of the standards, as related to particle size and density.

FIG. 12 illustrates variations in Two-Phase particles relationships between particle size and density. FIG. 12(a) illustrates a two-element overlap with each circle being a specific size and chemistry and FIG. 12(b) illustrates two adjacent elements each being of a specific size and chemistry.

DETAILED DESCRIPTION OF THE PREFERRED EMBODIMENTS

Figure 1A:
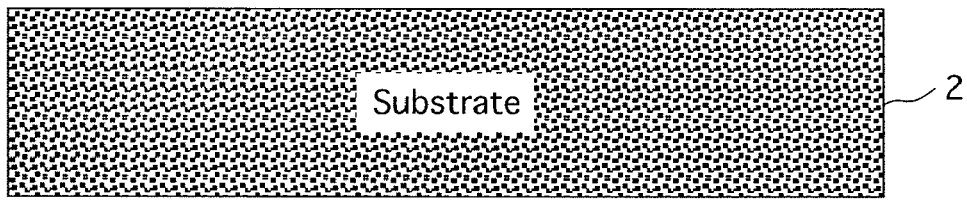
FIGS. 1(a)-1(i) show an example of a process of employing semiconductor fabrication technology in manufacturing a standard of the present invention.

As employed herein, the term "electron column tool" means any tool employing electron bombardment used to excite a sample from which responsive signals are produced, captured, and employed to determine morphology and/or chemistry of the sample.

As employed herein, the term "standard" means a structure which is bombarded with electrons or x-rays for purposes of calibrating an electron column tool and/or testing the same and/or testing a specimen.

Among the more important aspects of performance of standards are the following:

1. Image
   a. Resolution/Calibration
   b. Morphology
   c. Column/Stage
2. Chemistry
   a. Calibration
   b. Elemental Standards
   c. Accuracy of Analysis ZAF (wherein Z=atomic number, A=absorption, and F=florescence), bulk materials vs. particles vs. inclusions
3. Chemistry and Image (lithographic scanning, mapping, and phase identification)
4. Used in Development and Manufacturing
5. Used in Production (Customer)

Among the imaging modes which need to be taken into consideration are (1) secondary electron; (2) backscattered electron; (3) x-ray map, and (4) other electron or x-ray imaging modes.

Among the sample types to be emulated in the standard are (1) particles; (2) inclusions; (3) regions: phases, textures, microstructures; and (4) clusters: stringers.

Among the other considerations to be evaluated in the design and execution of the standards of the present invention are the materials must be electrical conductors or at least semiconductors. Conductive coatings may function effectively but may also present a maintenance issue. The materials must be stable in that they do not oxidize or react adversely with moisture. This may restrict the standard to a relatively small number of materials, such as, alumina, silica, chrome, nickel, gold, platinum, and some alloys. When using other metals or alloys that may oxidize the standard may be encapsulated with a thin cap of silicon nitride. The standards should be durable in order to resist accumulating surface debris and also need to be cleanable.

It is also important to bear in mind the end use of the standard and the specific need being addressed by the standard. For example, is the standard being done to develop/validate a specific analysis, such as GSR? Stringer analysis of a medical implant is an objective to demonstrate faster and more accurate results. Some of these considerations will assist with the determination of if the standard is calibration/standard-driven, such as one feature per known composition, features of known length and space, or time/count driven N copies of identical features) or distribution-driven (distribution of feature sizes, orientations, and compositions). These and use considerations contribute to determination of certain design parameters.

The imaging standard will be complex and designed specifically for the analysis applications outlined above, as well as lab requirements, which address specific needs are discussed below. These do not include more general needs, such as demonstration of speed or spectrometer calibration, which are covered by the overlapped metals and the high-density areas outlined further in RJ Lee Group analysis protocols. We want a high contrast such that the features are highly visible and not easily confused with surface debris. For example, surface debris in back scattered electrons images will be dark relative to background, so if features are brighter than the background, they will not be confused with surface debris.

Referring to FIGS. 1(a)-1(i), an example of the method of manufacturing a calibration of standard of the present invention employing semiconductor manufacturing technology will be considered. (Certain figures have been presented twice for clarity of illustration purposes.)

Figure 1B:
Figure 1B:
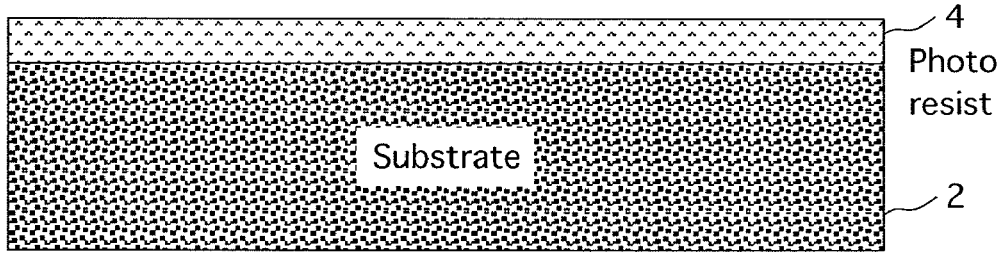
Figure 1C:
Figure 1C:
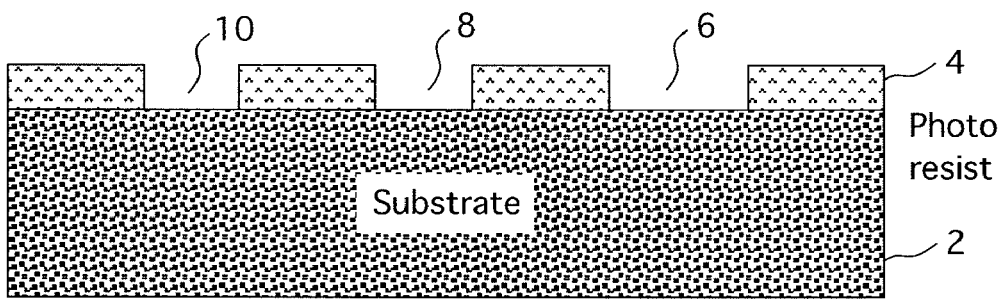

FIG. 1(a) shows a base or substrate 2, which may be a silicon wafer and may have the desired size and shape of the final standard. If desired, multiple units may be created on a silicon wafer and subsequently separated as by etching, for example. In FIG. 1(b), a photo resist 4 has been applied over the substrate 2. FIG. 1(c) shows the photo resist 4 after development to establish a plurality of openings 6, 8, 10.

Figure 1D:
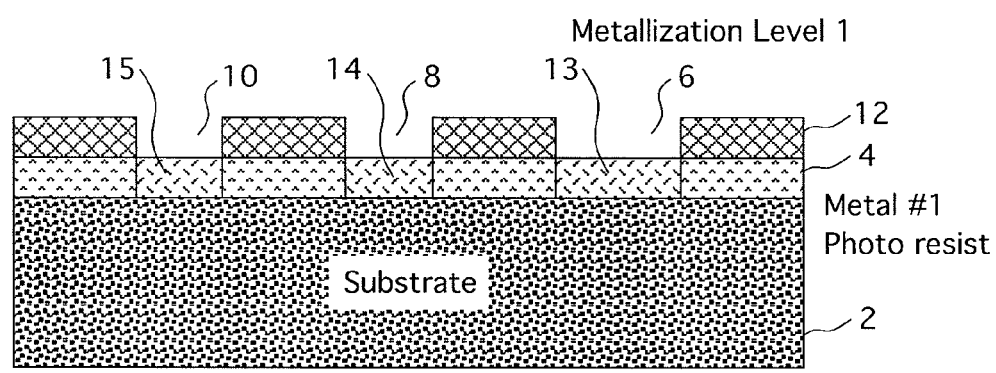

As shown in FIG. 1(d), metalization at level #1 provides metal sections, such as 12, overlying the photo resist and metal sections 13, 14, 15 positioned in voids, respectively, 6, 8, 10 disposed between adjacent segments of the photo resist.

Figure 1E:
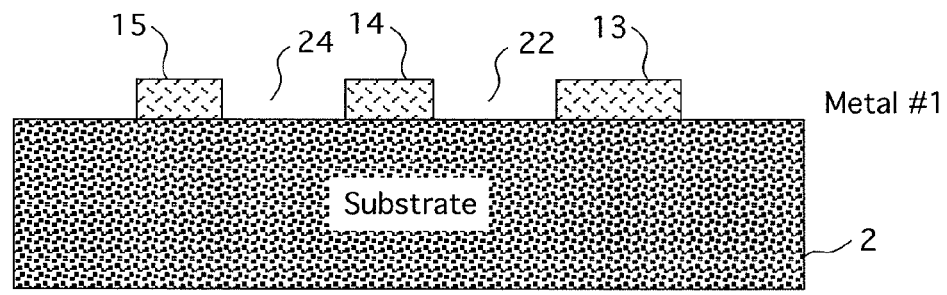

In FIG. 1(e), the metal #1 stacked portions 12 overlying photo resist 4 have been removed leaving metal #1 segments 13, 14, 15 in the desired pattern and location with spaces 22, 24 therebetween. It will be appreciated that, as will be described hereinafter, the desired patterns for the standard can be predetermined and established through this method.

Figure 1F:
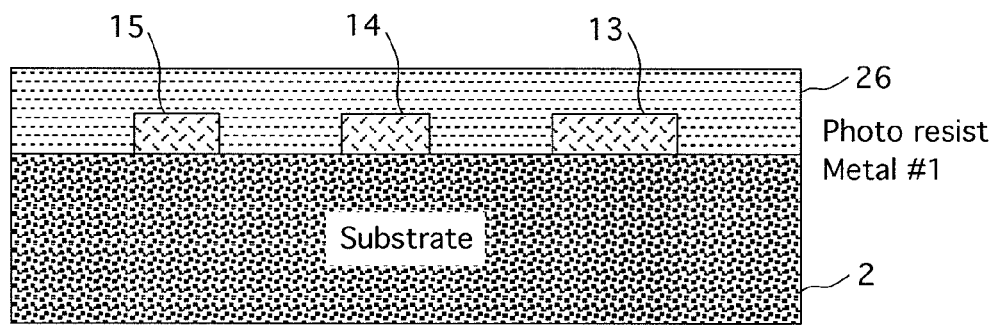

Referring to FIG. 1(f), a photo resist material 26 has been provided over metal #1 segments 13, 14, 15 and has filled in gaps, such as 22, 24, adjacent to the metal #1 segments 13, 14, 15.

Figure 1G:
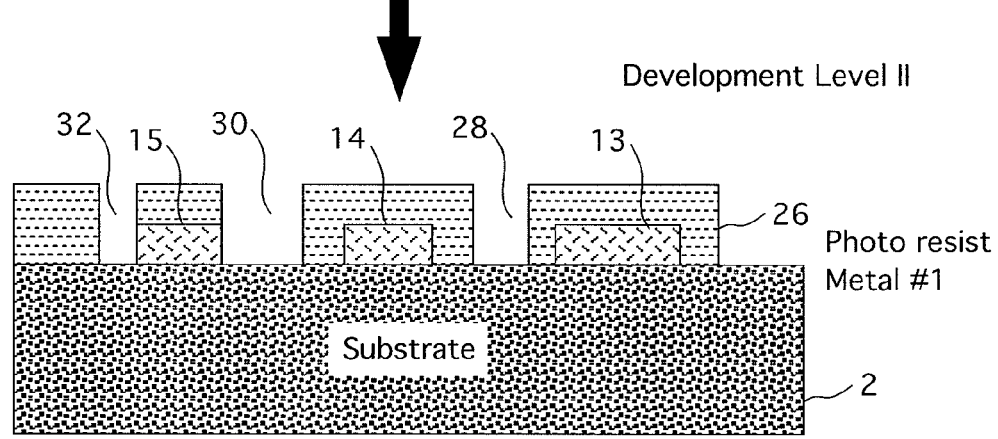

As shown in FIG. 1(g), portions of the photo resist have been removed to leave gaps 30, 32.

Figure 1H:
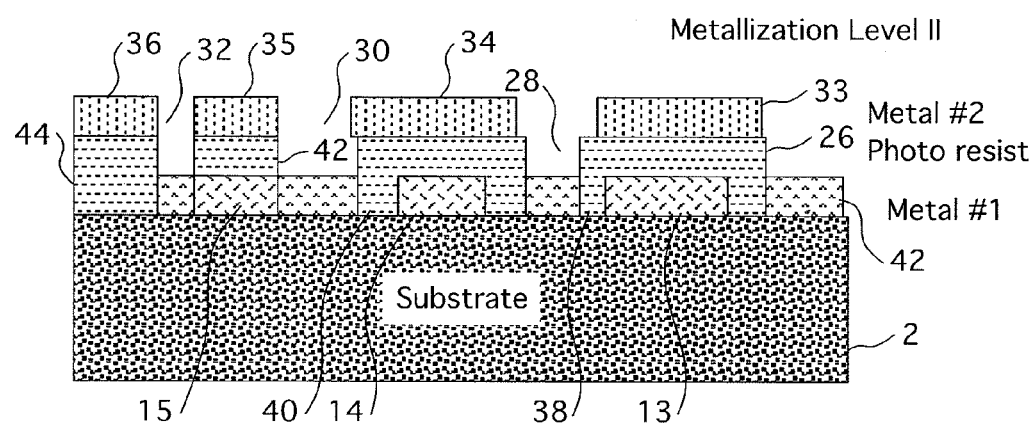

As shown in FIG. 1(h), metal #2 has been provided at locations 33, 34, 35, 36 overlying portions 38, 40, 42, 44 of photo resist 26. A layer 42 of the second metal is present on exposed portions of substrate 2.

Figure 1I:
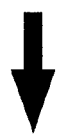
Figure 1I:
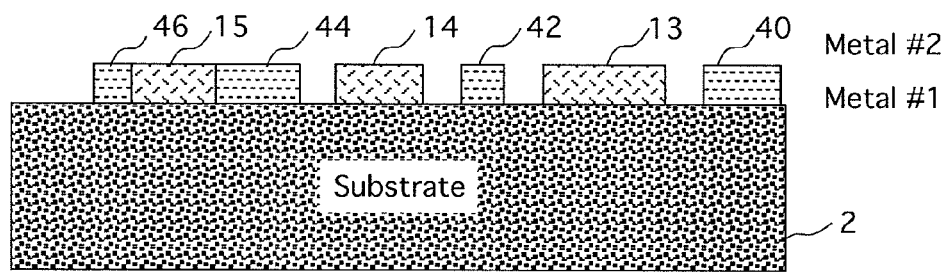

Referring to FIG. 1(i), the photo resist 26 and the metal #2 overlying the same (FIG. 1(h)) have been removed, thereby leaving substrate 2 with portions of metal #1 segments 13, 14, 15 overlying the same and metal #2 portions 40, 42, 44, 46 also overlying and secured to the substrate 2 and adjacent to portions of metal #1. It will be appreciated that employing known semiconductor fabrication technology once the structure of the standard has been defined, these techniques can be used to manufacture the same.

Figure 2:
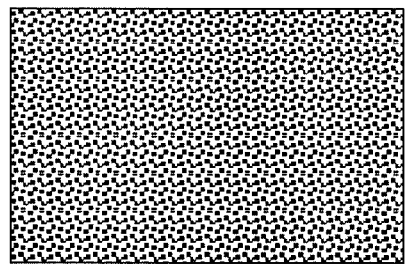
FIG. 2 is a schematic illustration of a form of standard of the present invention illustrating pixel spacing and resolution.

The following are among significant imaging needs to be addressed: (a) pixel spacing/resolution; (b) computer-controlled SEM (CCSEM) analysis assumes that features can be detected using a search grid that is significantly coarser than feature size, and that the results can be scaled to correct for missed features by knowing the exact parameters of the standard during verification tests. The accuracy of this assumption needs to be tested, demonstrated, and quantified using a large number of identical features with random (known) spatial locations. See FIG. 2.

Figure 3:
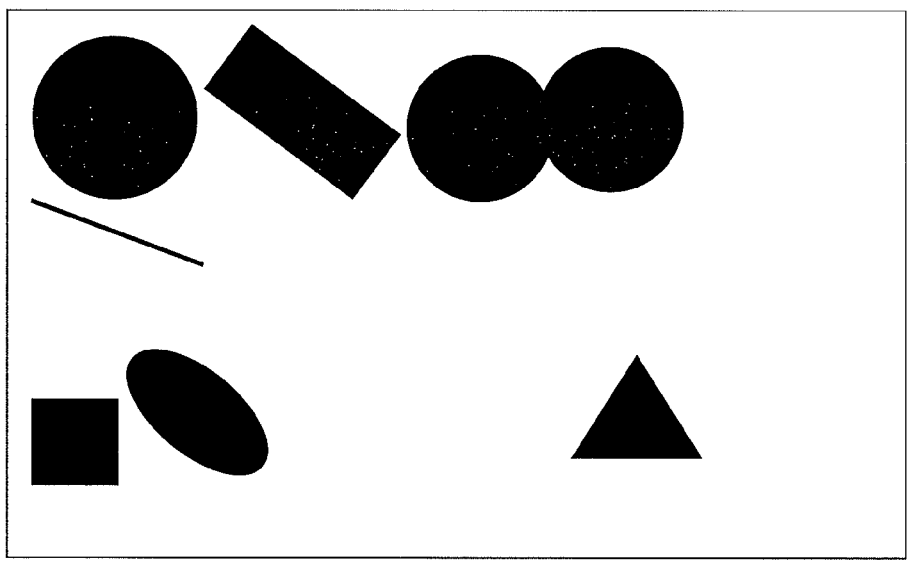
FIG. 3 is a schematic illustration of examples of various shapes and relative positions.

Among the feature attributes are the accuracy of feature parameters. The accuracy of feature parameters, e.g., area, diameter, perimeter, shape factors, orientation, needs to be quantified using collections of spheres, ellipses, squares, rectangles, triangles and lines. See FIG. 3.

Figure 4:
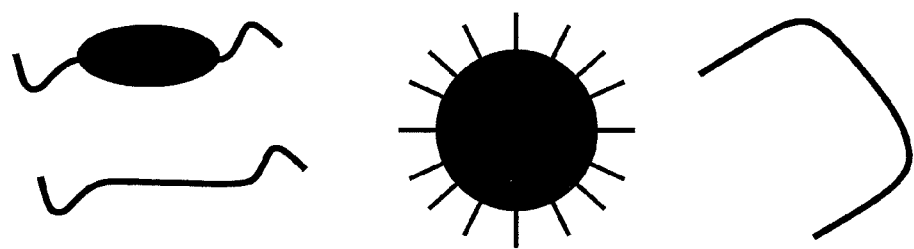
FIG. 4 is an illustration of several forms of pathological shapes.

Pathological shapes can have an influence on standard design. The standard may have the ability to correctly measure the attributes of fibers, concave objects, and aggregated features. This is especially important for elongation (used in medical implant wear studies). See FIG. 4.

Figure 5:
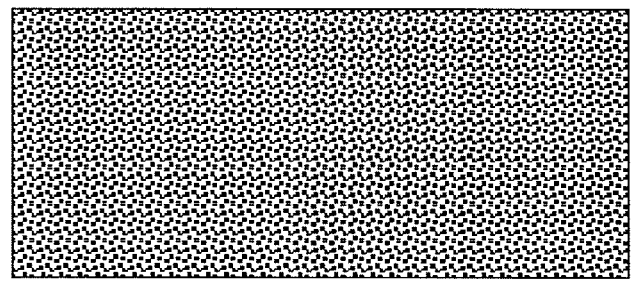
FIG. 5 is a schematic illustration of a SEM standard with a large array of space density in particular.

Column/stage is preferred to employ a large aligned array of features to quantify image rotation (column issue) and stage travel. See FIG. 5. While there is no critical dimension for the standard size, they may be on the order or about 1 cm$^2$ to 3 mm for SEM to STEM, respectively.

Figure 6A:
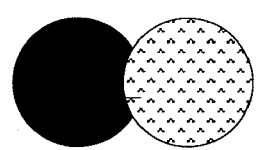
FIGS. 6(a) and 6(b) show, respectively, a two-element overlap with each circle being a specific size and chemistry and two adjacent elements each being of a specific size and chemistry
Figure 6B:
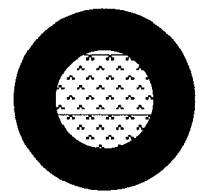

Among the important, combined image/chemistry needs to be addressed are lithographic scanning, which can be verified and demonstrated using several complex features, such as aggregates and inclusions of features with different chemistries. FIGS. 6(a) and 6(b) show a two-element overlap with each circle being a specific size and chemistry and two adjacent elements each being of a specific size and chemistry.

Figure 7:
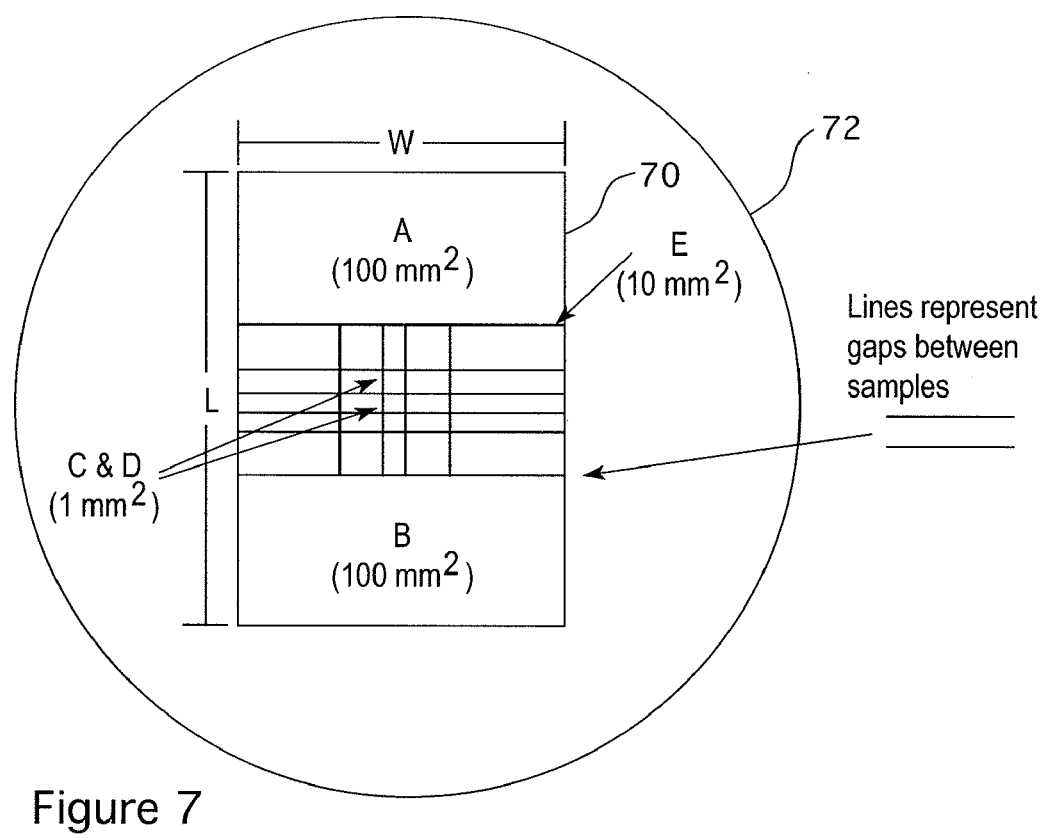
FIG. 7 is a representation of a standard of the present invention illustrating different zones having different characteristics.

FIG. 7 shows the generally-rectangular standard 70 disposed on a support 72. The standard has a width W, which may be about 1 cm to 2 cm and a length L, which may be about 3 cm to 4 cm. Although, the size will generally be dictated by the particular environment, regions A-E, shown in FIG. 7, correspond, respectively, to Tables 1-5 and FIGS. 8-12.

Figure 8:
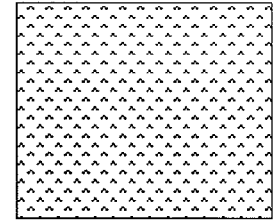

The number of fields employed in the standard may advantageously be related to the size of the particle being analyzed with the use of more fields for smaller particles being preferred. It will be appreciated, therefore, that FIG. 7 shows a single standard 70 having various zones associated with the size of particles being analyzed. FIG. 8, for example, illustrates a standard having large particles at low density. The particle size and number of particles are shown in Table 1.

Figure 9:
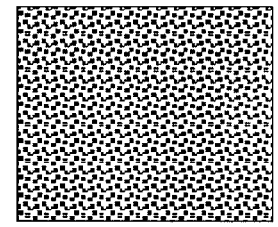

Table 2 and FIG. 9 are directed toward large particles with high density.

Figure 10:
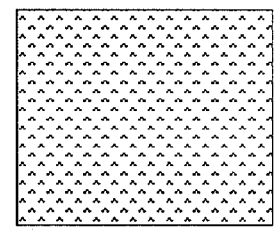

Table 3 and FIG. 10 relate to small particles with low density.

Table 4 and FIG. 11 are directed toward small particles with high density.

Table No. 5 and FIGS. 12(a) and 12(b) illustrate two-phase particles.

Other regions on the standard 70 can be used for EDX (EDS energy dispersive x-ray or spectrometer) calibration tests and application-specific samples, e.g., medical device wear debris.

Metals will be placed with features in a periodic and known spacing, so that various sizes and shapes can be located with specific metals. Metals may be chosen from the following list: C, O, N, AL, Si, Ti, Cr, Cu and others to be determined.

The C and D (Tables 3 and 4 and FIGS. 10 and 11) models may have circular and rectangular regions of the appropriate size to conform to the specified TEM (transmission electron microscope)/STEM (scanning transmission electron microscope) holders. These may be etched from the backside to be appropriately thinned for STEM use.

The approach of the present invention will allow this standard design to be used for other analytical techniques and technologies, including, but to not limited to, XPS (x-ray photoelectron spectroscopy), XRF (x-ray florescence), and other types of spectrometers. The present invention permits the use of a single standard which can be analyzed in a wide range of spectrometers, enabling RJ Lee's diverse laboratory to emphasize speed, accuracy and cross-tool advantages.

Whereas particular embodiments of the present invention have been described herein for purpose of illustration, it will be evident to those skilled in the art that numerous variations of the details may be made without departing from the invention, as set forth in the appended claims.

What is claimed is:

1. A standard for use in particle analysis by way of electron column tools comprising
   a semiconductor standard structured to provide simultaneous morphology and chemistry information with respect to particles being analyzed.

2. The standard for use in particle analysis by way of electron column tools of claim 1 including
   said standard having portions structured to evaluate size, shape, chemistry, and location.

3. The standard for use in particle analysis by way of electron column tools of claim 1 including
   said standard being structured to be modified in order to be employed with different electron column tools.

4. The standard for use in particle analysis by way of electron column tools of claim 3 including
   said standard being structured to be employed with scanning transmission electron microscopes.

* * * * *

UNITED STATES PATENT AND TRADEMARK OFFICE
CERTIFICATE OF CORRECTION

PATENT NO. : 8,138,470 B2  
APPLICATION NO. : 12/720200  
DATED : March 20, 2012  
INVENTOR(S) : John Mastovich Page 1 of 1

It is certified that error appears in the above-identified patent and that said Letters Patent is hereby corrected as shown below:

Column 2, line 8, "chemistry" should read --chemistry.--.
Column 2, line 42, "F=florescence" should read --F=fluorescence--.
Column 2, line 57, "are the materials" should read --are that the materials--.
Column 3, line 7, "determination of if" should read --determination if--.
Column 3, line 16, "needs are" should read --needs as are--.
Column 3, line 23, "electrons images" should read --electron images--.
Column 4, line 25, "order or" should read --order of--.
Column 5, line 5, "but to not," should read --but not,--.
Column 5, line 6, "florescence" should read --fluorescence--.
Column 5, line 12, "for purpose of" should read --for purposes of--.

Signed and Sealed this
Eighth Day of May, 2012

David J. Kappos
*Director of the United States Patent and Trademark Office*